United States Patent
Forster (10) Patent No.: US 8,872,663 B2
(45) Date of Patent: Oct. 28, 2014

(54) MEDICATION REGIMEN COMPLIANCE MONITORING SYSTEMS AND METHODS

(75) Inventor: Ian J. Forster, Essex (GB)

(73) Assignee: Avery Dennison Corporation, Glendale, CA (US)

(*) Notice: Subject to any disclaimer, the term of this patent is extended or adjusted under 35 U.S.C. 154(b) by 554 days.

(21) Appl. No.: 12/689,257

(22) Filed: Jan. 19, 2010

(65) Prior Publication Data

US 2011/0175735 A1 Jul. 21, 2011

(51) Int. Cl.
*G08B 23/00* (2006.01)
*A61B 5/00* (2006.01)

(52) U.S. Cl.
CPC ....... *A61B 5/6833* (2013.01); *A61B 2560/0412* (2013.01); *A61B 5/002* (2013.01); *A61B 5/4833* (2013.01)
USPC ....................................... 340/573.1; 600/301

(58) Field of Classification Search
CPC . G01K 13/00; G06K 19/0717; A61B 5/00243
USPC .................................................. 600/300, 301
See application file for complete search history.

(56) References Cited

U.S. PATENT DOCUMENTS 7,486,977 B2 * 2/2009 Sweitzer et al. .............. 600/323
7,820,108 B2 * 10/2010 Lampotang et al. ............ 422/84
2006/0290496 A1 * 12/2006 Peeters ...................... 340/572.1
2007/0089335 A1 4/2007 Smith et al.
2007/0100218 A1 5/2007 Sweitzer et al.
2007/0226142 A1 * 9/2007 Hanna et al. .................... 705/41
2007/0258894 A1 11/2007 Melker et al.

FOREIGN PATENT DOCUMENTS

| EP | 0396788 | 11/1990 |
|---|---|---|
| WO | WO2008008899 | 1/2008 |
| WO | WO2009036334 | 3/2009 |
| WO | WO2009105337 | 8/2009 |

OTHER PUBLICATIONS

PCT/US2011/021057; 4776-PC; Transmittal of International Search Report and The Written Opinion of the International Searching Authority; Aug. 17, 2011.

* cited by examiner

*Primary Examiner* — Steven Lim
*Assistant Examiner* — Omeed Alizada
(74) *Attorney, Agent, or Firm* — Avery Dennison Corporation (57) ABSTRACT

A system for monitoring compliance with a medication regimen comprises a patch. The patch includes an RFID apparatus and a sensor. The patch is configured to be removably securable to a body of a biological organism. The sensor is in electrical communication with the RFID apparatus and is configured to inspect a biological material of a biological organism for the presence of a detectable agent. The RFID apparatus is configured to communicate a result of the inspection to an RFID transceiver and/or a communication device. Methods are also provided.

29 Claims, 4 Drawing Sheets

MEDICATION REGIMEN COMPLIANCE MONITORING SYSTEMS AND METHODS

TECHNICAL FIELD OF THE INVENTION

The present invention relates generally to the monitoring of a person's compliance with a prescribed medication regimen and more particularly to monitoring a person's compliance with a prescribed medication regimen by sensing a detectable agent ingested with medication or a part of a dietary arrangement.

BACKGROUND OF THE INVENTION

Medical professionals often treat patients by prescribing a medication regimen designed to improve or stabilize a medical condition, ensure compliance with a court ordered rehabilitation program, to maintain the quality of life or to provide relief after the patient has suffered a trauma or is undergoing late stage illness treatment. A medication regimen typically includes instructions for a patient to ingest a prescribed medication at a specific dosage and at prescribed time intervals. The effectiveness of such medication regimens often depends on how well the patient complies with the instructions of the regimen. For example, if the patient does not ingest the medication at the prescribed time intervals or dosage, the medication regimen may be ineffective or even harmful to the patient.

Current arrangement exist to sense the presence that a pill or other medication has been removed from a package, e.g. a pill container, but such systems do not confirm whether the patient or subject does not take the medicine and has merely removed the medicine from the container in order to show the removal.

Patients or program recipients can fail to adhere to a medication or other dosage regimen for a variety of reasons. For example, elderly patients often forget to take medication or become confused because of the complexity of simultaneously taking multiple medications or adhering to multiple medication regimens or changing dosage requirements, e.g. increasing or decreasing the amounts of the medication. As another example, patients often fail to adhere to medication regimens because of the cost of a particular medication or combination of medications, fear of side-effects, underestimating the severity of a medical condition, misunderstanding instructions or just a general desire not to take the medication. Failure to adhere to a medication regimen can result in prolonged recovery time, deterioration of the medical condition, increased risk of new medical problems, increased medical costs or other undesired or unintended consequences.

What is needed therefore is a system to confirm compliance with a medication regimen in order to further the well being of the patient.

SUMMARY OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In accordance with one embodiment, a system for monitoring compliance with a medication regimen comprises a patch and an RFID transceiver. The patch includes an RFID apparatus and a sensor. The patch is configured to be removably securable to a body of a biological organism. The sensor is in electrical communication with the RFID apparatus and is configured to inspect a biological material of a biological organism for the presence of a detectable agent. The RFID apparatus is configured to communicate a result of the inspection to the RFID transceiver.

In accordance with another embodiment, a system for monitoring compliance with a medication regimen comprises a patch and a communication device. The patch includes an RFID apparatus and a sensor. The patch is configured to be removably securable to a body of a biological organism. The sensor is in electrical communication with the RFID apparatus and is configured to inspect a biological material of a biological organism for the presence of a detectable agent. The RFID apparatus is configured to communicate a result of the inspection to the communication device. The communication device is configured to receive the results of the inspection and is further configured to transmit the results of the inspection to a remote location.

In accordance with another embodiment, a method is provided for monitoring compliance with a medication regimen. The method comprises positioning a sensor proximate to a biological organism, where the sensor is in electrical communication with an RFID apparatus. The method further comprises using the sensor to inspect a biological material of a biological organism for the presence of a detectable agent. The method further comprises transmitting with the RFID apparatus a result of the inspection to an RFID transceiver.

In accordance with another embodiment, a method is provided for monitoring compliance with a medication regimen. The method comprises positioning a sensor proximate to a biological organism, where the sensor is in electrical communication with an RFID apparatus. The method further comprises using the sensor to inspect a biological material of a biological organism for the presence of a detectable agent. The method further comprises transmitting with the RFID apparatus a result of the inspection to a communication device. The method further comprises transmitting with the communication device the result of the inspection to a remote location.

In the foregoing embodiments, the detectable agent can include a dietary supplement, ingestible trace element, food that produces a particular chemical based on the genetic make up of the individual (e.g. dairy products, asparagus, other fruits or vegetables, high sugar foods, and the like).

Other features and advantages of the present invention will become apparent to those skilled in the art from the following detailed description. It is to be understood, however, that the detailed description of the various embodiments and specific examples, while indicating preferred and other embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which.

DETAILED DESCRIPTION OF THE INVENTION

The apparatuses and methods disclosed in this document are described in detail by way of examples and with reference to the figures. Unless otherwise specified, like numbers in figures indicate references to the same, similar, or corresponding elements throughout the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be and should not be construed as mandatory or limiting unless specifically designated as such. Selected examples of apparatuses and methods for monitoring compliance with a medication regimen are hereinafter disclosed and described in detail with reference made to FIGS. 1-3.

Medication regimen compliance monitoring can include monitoring a biological organism, such as a human, for compliance with one or more medication regimens. A medication regimen can include instructions to ingest a specific drug or medication at specific times over the course of a treatment cycle. For example, a medical professional can examine a patient and diagnose the patient as having an infection. One course of treatment can be to prescribe a medication regimen for the patient, where the regimen includes ingesting a pill, capsule, liquid or other suitable form of medication that includes an antibiotic agent to combat the infection. The medication regimen can, for example, include instructing the patient to ingest a pill twice a day, once in the morning and once in the evening, for ten days.

Monitoring the patient's compliance with such a medication regimen can include apparatuses and methods for detecting whether and when the patient has ingested the specific medication, determining from such detections whether the patient is in compliance with the medication regimen, storing data related to such detections and compliance determinations, and/or transmitting such detections and compliance data to remote locations. By determining compliance or non-compliance with the medication regimen, a medical professional who is treating the patient or a caregiver interested in the health of the patient can take an action that is appropriate for the benefit of the patient.

It will be understood that monitoring a person's compliance with medication regimens can not only be beneficial to the person, but can be beneficial to those that come into contact with the person. For example, it is beneficial to determine if a person with a contagious disease such as tuberculosis or a person taking antipsychotic medication is complying with prescribed medication regimens. In addition, it may be beneficial for habitual drug, alcohol or sex offenders to be monitored to ensure the medication is being timely taken so as to reduce their risk to the local citizenry.

In one example, medication can include a detectable agent to assist in facilitating monitoring of medication regimen compliance. The detectable agent can be arranged such that, when the medication is ingested and metabolized, the detectable agent can produce a characteristic chemical marker or signature that is detectable by inspecting a person's biological materials. In another example, the detectable agent itself can be a chemical marker or signature that is detectable by inspecting a person's biological materials, and without need for metabolization of the detectable agent. In one example, a detectable agent can be a food component that is distinct from the person's regular diet. For example, the detectable agent can be a particular food, such as fruits or vegetables (e.g. asparagus) dairy product, sugary foods or food-safe additive such as a protein, oil, flavoring, or other suitable chemical that is generally benign to the person. Volatile organic compounds that can be responsible for eliciting a particular detectable agent include methanethio, dimethyl sulfide, dimethyl disulfide, bis(methyllithio)methane, dimethyl sulfoxide, dimethyl sulfone, other sulfur containing degradation products including various thiols, thioesters and ammonia. Examples of biological materials that can be inspected for the presence of the detectable agents or chemical markers include the person's perspiration, exhalations, blood, tears, urine, excretions and saliva, among others.

Apparatuses can be positioned proximate to a body of the person to sense or detect the detectable agent through inspection of biological materials. Once the presence or absence of the detectable agent is sensed, such apparatuses can determine compliance or non-compliance with a medication regimen, store data, and/or transmit such data to local or remote locations to assist the monitoring location whether some intervention is required. Monitoring compliance with medication regimens from a remote location can increase the frequency, efficiency, and usefulness of such monitoring. For example, a medical professional or caregiver can more frequently monitor the person's compliance with a medication regimen through remote monitoring. Remote monitoring can alert the medical professional or caregiver when the person is not complying with a medication regimen and corrective action, such as initiating of a reminder or making an in-home visit, can be taken to benefit the person.

Figure 1:
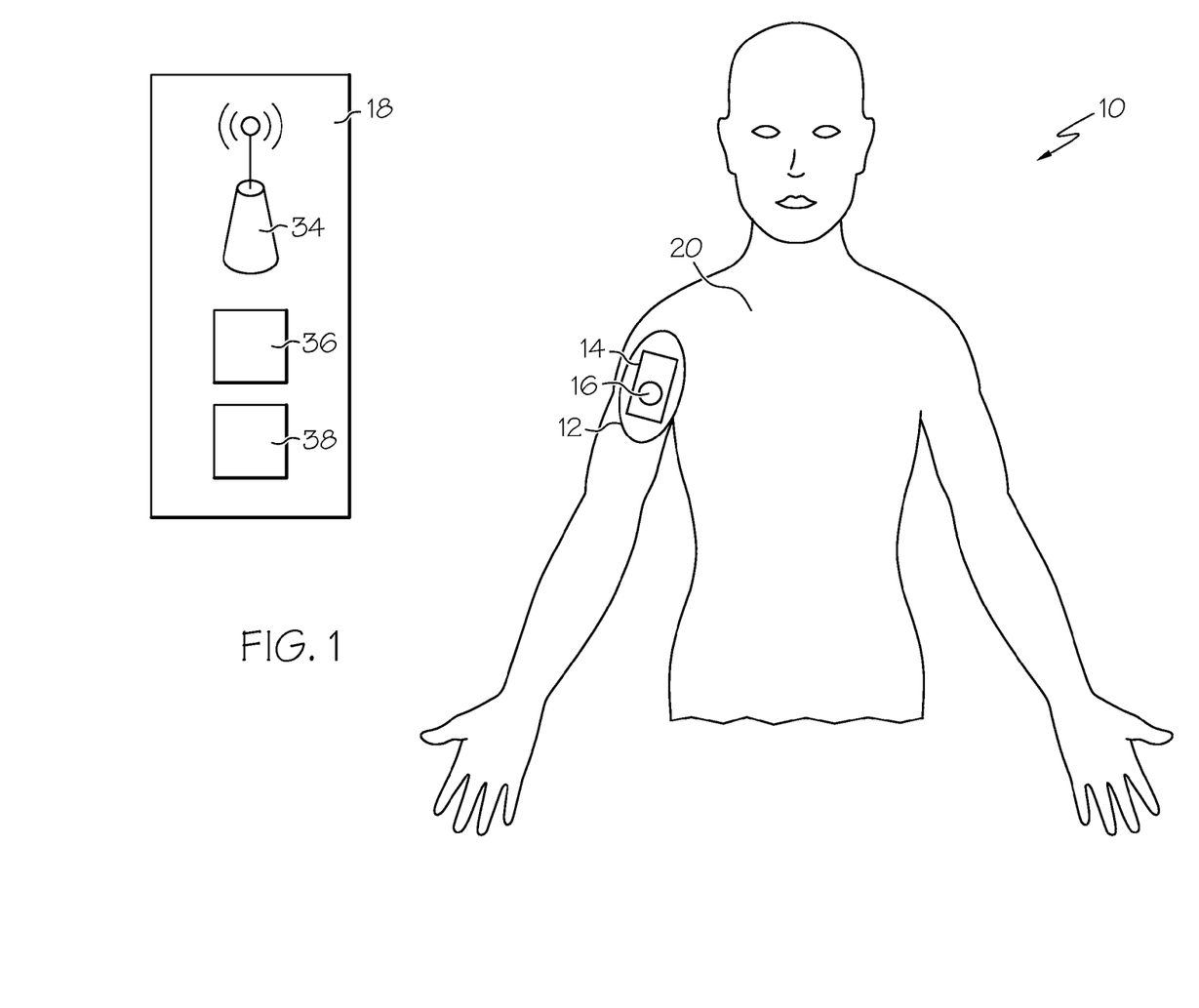
FIG. 1 is a schematic view depicting a system for monitoring compliance with a medication regimen in accordance with one embodiment, wherein a patch is removably secured to a human and includes an RFID apparatus that communicates with an RFID transceiver.

As schematically illustrated in FIG. 1, one example of a medication regimen monitoring system 10 can comprise a patch 12 and a radio frequency identification (RFID) transceiver 18.

The patch 12 can be configured to include an RFID apparatus 14 and a sensor 16. Exemplary RFID devices available for use in practicing the present invention are available from Avery Dennison RFID Company of Flowery Branch, Ga. As will be further described, the RFID apparatus 14 and/or sensor 16 can be configured to facilitate inspection of a person's biological materials to monitor the person's compliance with medication regimens. In one example, the patch 12 can be configured to be removably secured to the person's body 20, such as through the use of removable or repositionable adhesives, to facilitate the inspection of biological materials located on or near the surface of the person's skin. For example, a patch 12 can be removably secured to the person's skin so that the RFID apparatus 14 and/or sensor 16 can inspect the person's perspiration or blood for a detectable agent included in medication. As shown in FIG. 1, in one example, the patch 12 can be adhered to an upper arm of the person's body 20 to position the RFID apparatus 14 and/or sensor 16 in contact or close proximity to the person's skin.

In another example, the patch 12 can be positioned near, but not directly on, the person's body 20 so as to facilitate inspecting of the person's biological materials. For example, the patch 12 can be secured to the person's clothing proximate to the person's mouth such that the RFID apparatus 14 and/or sensor 16 can inspect the person's exhalations for detectable agents included in medication. As will be further described, once the person's biological materials are inspected to detect the presence or absence of detectable agents, the RFID apparatus 14 can communicate such detections to one or more other devices, such as the RFID transceiver 18.

Figure 2:
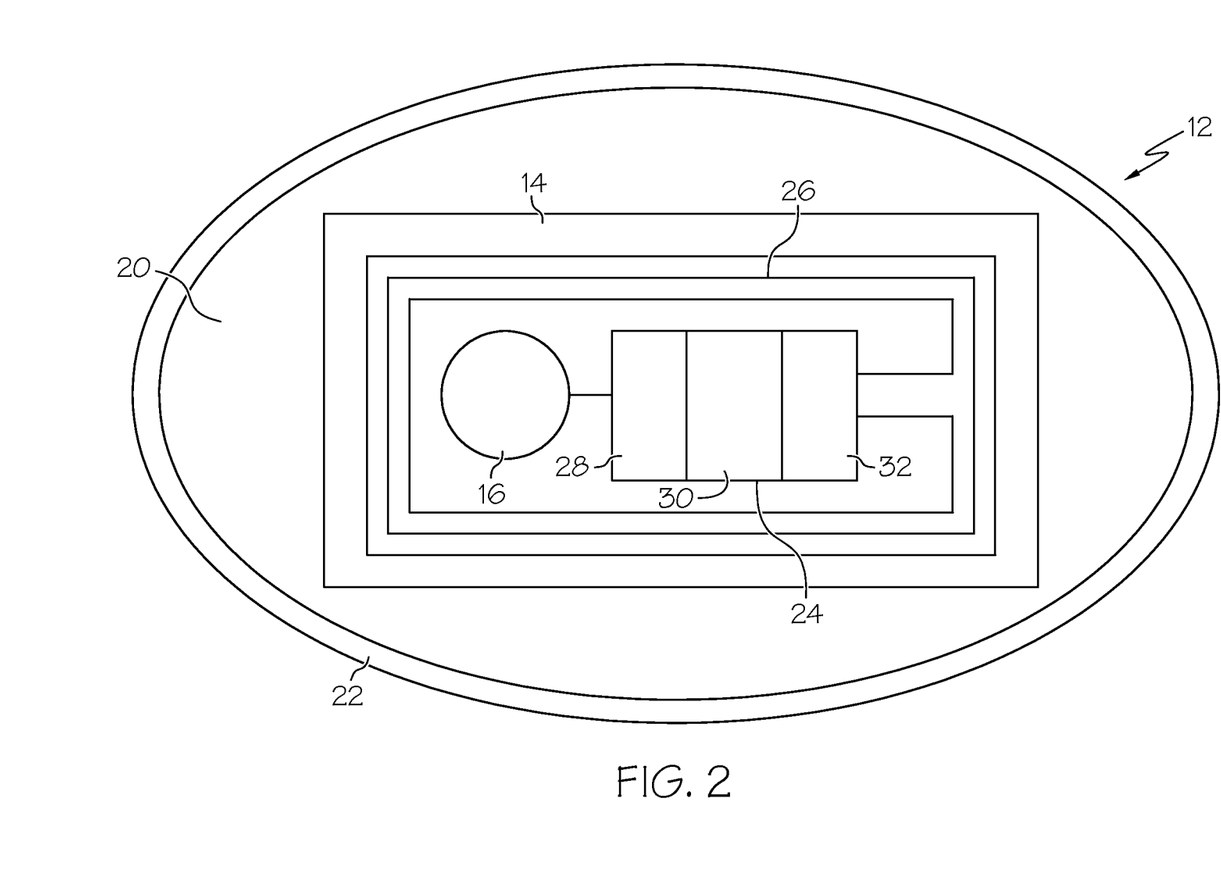
FIG. 2 is a schematic view depicting the patch of FIG. 1.

FIG. 2 schematically illustrates the patch 12 in further detail. In addition to the RFID apparatus 14 and sensor 16, the patch 12 can include an adhesive portion 22. The adhesive portion 22 can be configured to removably secure the patch 12 to the person's body 20. The RFID apparatus 14 can include an RFID chip 24 and an antenna 26 in electrical communication with the RFID chip 24. The RFID apparatus 14 and the RFID transceiver 18 can be configured to communicate with one another. For example, the RFID transceiver 18 can be configured to transmit radio signals encoded with data or instructions to the RFID apparatus 14. The antenna 26 can be configured to receive such radio signals and relay the radio signals to the RFID chip 24. The RFID chip 24 can be configured to interpret instructions encoded in the radio signals broadcast by the RFID transceiver 18.

The RFID device can be further configured to include a visual display or to generate an audible tone based on the results of the inspection, or to signal the current status of the device.

In one example, the RFID chip 24 can be a high-frequency (HF) RFID chip 24 with a unique identifier to facilitate communications between the RFID apparatus 14 and the RFID transceiver 18 or other such suitable devices. Alternatively, the RFID device can operate in the ultra high frequency range (UHF) or low frequency range (LF). In another example, the RFID apparatus 14 can be configured to generate its own radio signals, or the RFID apparatus can be configured to receive radio signals from the RFID transceiver 18 and reflect the radio signals back to the RFID transceiver 18 to facilitate communications. The RFID chip 24 can encode such radio signals with data or instructions. For example, the RFID chip 24 can encode the radio signal with data corresponding to the detection or absence of detectable agents in the person's biological material. In another example, the RFID chip 24 can encode the radio signal with the unique identifier so that any device receiving radio signals from the RFID chip 24 can ascertain the source of the radio signal. The RFID transceiver 18 can be configured to receive radio signals from the RFID apparatus 14 and interpret data, instructions, unique identifiers, and the like encoded in the radio signals.

The sensor 16 can be configured to inspect the person's biological materials to directly or indirectly determine the presence of the detectable agent in the biological materials. As previously discussed, the presence of chemical markers in biological materials can be indicative of the detectable agent included in medication. The sensor 16 can be configured to be in electrical communication with the RFID chip 24. In such a configuration, the sensor 16 can relay readings or detections of detectable agents or chemical markers to the RFID chip 24. The RFID chip 24 can in turn communicate such readings or detections to the RFID transceiver 18 by encoding such detections in radio signals broadcast to the RFID transceiver 18. The sensor 16 can be configured in a number of arrangements to detect detectable agents or chemical markers depending on the biological materials inspected. For example, if blood is to be inspected, the sensor 16 can include an infrared radiation source or a light emitting diode to inspect the capillaries near the surface of the person's skin to determine if the chemical marker is present. In another example, if the person's perspiration is to be inspected, the sensor 16 can measure electrical resistance in order to detect the presence or absence of the detectable agent or chemical marker as indicated by changes in the resistivity of the person's perspiration.

With reference to FIG. 2, in one example, the RFID chip 24 can comprise an RFID tag portion 28, a memory portion 30, and a power source 32. It will be understood that, in other examples, an RFID apparatus might include only an RFID tag portion, such as when the RFID tag portion is a passive tag. In still other examples, an RFID apparatus might only include an RFID tag portion and a memory portion. In still other examples, an RFID apparatus might include only an RFID tag portion and a power source. It will be understood that the RFID apparatus 14 can be configured in any of a variety of suitable arrangements to manage detections or readings ascertained by the sensor 16.

In one example, the memory portion 30 can be configured to store detections acquired by the sensor 16. For example, the memory portion 30 can be configured to periodically store the detection or absence of a chemical marker in the person's biological material as measured by the sensor 16. A collection of stored detections can represent the compliance profile of the patient over a period of time. Such a compliance profile can be useful in determining the long-term compliance of the patient with the medication regimen.

In one example, the power source 32 can provide power to the RFID apparatus 14 so that the RFID apparatus 14 operates as an active RFID tag. The power source 32 can comprise, for example, a battery, a supercapacitor, power antenna or other such suitable source of power. When the RFID apparatus 14 operates as an active RFID tag, the RFID apparatus 14 can transmit radio signals using power from the power source 32. In another example, the power source 32 can be configured to provide power to the sensor 16 so that the sensor 16 can inspect biological materials for the presence or absence of detectable agents or chemical markers. It will be appreciated that, in an alternative embodiment, the sensor 16 can be powered by its own power source dedicated to powering the sensor 16.

In one example, the RFID apparatus 14 can include an integrated circuit. The integrated circuit can include the RFID tag portion 28 and the memory portion 30. In such a configuration, the integrated circuit can be configured to store data, instructions, information, and the like. The integrated circuit can further be configured to process or manage data and information, modulate and demodulate a radio signal, and other such functions. The antenna 26 can be in electrical communication with the integrated circuit and can be configured to transmit and receive radio signals. In addition, the RFID apparatus 14 can be configured to include HF or UHF inlays and/or can be configured to amplify a passive RFID tag portion.

Referring again to FIG. 1, the RFID transceiver 18 can include a radio signal transmitter 34 that can transmit radio signals. The radio signal transmitter 34 can send a radio signal to the RFID apparatus 14 encoded with instructions. For example, the RFID transceiver 18 can instruct the RFID apparatus 14 to initiate the inspection of the person's biological material by the sensor 16 and to return data indicative of the results of such inspections. In another example, the RFID transceiver 18 can instruct the RFID apparatus 14 to send data stored on the memory portion 30 of the RFID apparatus 14 back to the RFID transceiver 18. In such an arrangement, the RFID transceiver 18 can function as an RFID reader, and the RFID apparatus 14 can use power from the power source 32 to broadcast radio signals encoded with data to the RFID transceiver 18.

The RFID transceiver 18 can also function as a source of energy for the RFID apparatus 14. For example, the RFID transmitter 18 can transmit relatively high energy radio signals that can be received by the antenna 26 and captured by the RFID tag portion 28. The energy from the radio signals can then be directed to power the RFID apparatus 14 and/or the sensor 16. When the RFID tag portion 28 is configured as a passive tag, such high energy radio signals can be modulated by the RFID tag portion 28, encoded with data from the sensor 16 and/or memory portion 30, and reflected back to the RFID transceiver 18. In such an example, the RFID transceiver 18 can control the operation of the sensor 16 and RFID apparatus 14, and without need for the RFID apparatus 14 to include a power source such as 32. It will accordingly be understood that the RFID transceiver 18 can initiate the inspection of the person's biological materials.

In one example, the RFID transceiver 18 can be positioned in a patient's home and function as an RFID reader. For example, for an elderly person, the RFID transceiver 18 can be positioned at a location frequented by the person, such as proximate to an armchair in which the elderly person typically sits during the day. The RFID transceiver 18 can be configured so that it initiates an inspection of the person's biological material each time the patient comes within range of the RFID transceiver 18. For example, the RFID transmitter 18 can be placed within an armrest of the armchair, and can initiate a reading whenever it detects a vibration or pressure applied to the armchair, indicating that the person is seated in the armchair.

As illustrated in FIG. 1, in one example, the RFID transceiver 18 can include a memory portion 36. The memory portion 36 can be configured to store data received from the RFID apparatus 14. For example, the memory portion 36 can store the results of successive inspections of the person's biological material as performed by the sensor 16 and transmitted by the RFID apparatus 14. Such a collection of measurements can represent a compliance profile of the person's adherence to the medication regimen over a period of time.

The RFID transceiver 18 can further include an internal communication component 38 such as a cell phone, internet connection, landline connection, or other suitable devices for transmitting information. The communication component 38 can be configured to send alerts or data regarding the person's compliance with the medication regimen to remote locations such as a doctor's office, a caregiver, a server that compiles a person's electronic medical record, etc. It will be understood that the sending of such data can result in early detection of a person's lack of compliance with the medication regimen. Such early detection can initiate an intervention that can prompt the person to become compliant with the medication regimen.

Figure 3:
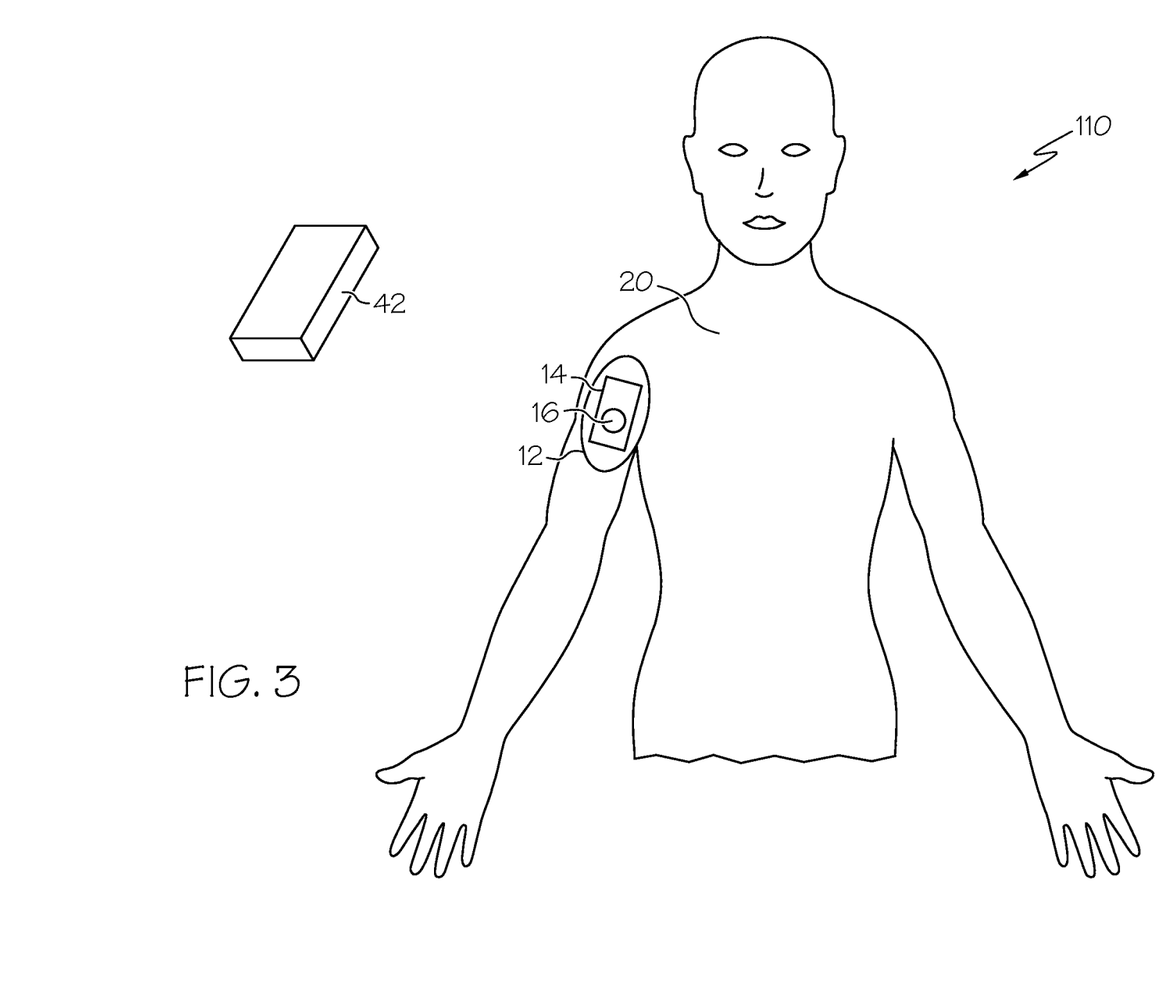
FIG. 3 is a schematic view depicting a system for monitoring compliance with a medication regimen in accordance with another embodiment, wherein a patch is removably secured to a human and includes an RFID apparatus that communicates with a communication device.

Another example of a medication regimen monitoring system 110 is schematically illustrated in FIG. 3. The medication regimen monitoring system 110 includes the patch 12 and a communication device 42. The patch 12 can be generally as described above, and can include the RFID apparatus 14 and sensor 16. The RFID apparatus 14 can be configured to communicate information regarding the detection of detectable agents or chemical markers in the person's biological matter to the communication device 42. The communication device 42 in turn can be configured to receive or otherwise capture the information communicated by the RFID apparatus 14. In one example, the RFID apparatus 14 and the communication device 42 can communicate with one another through wireless communication technology such as, for example, near field communication, short-range radio frequency communication system (such as those that operate on standards such as the IEEE 802 family of wireless communication protocols, including 802.11x and 802.15), and infrared signal communication, among others.

In one example, the communication device 42 can comprise a mobile phone or personal digital assistant equipped with near field communication capabilities. The RFID apparatus 14 can include a 13.56 MHz RFID tag to communicate with the near-field-capable communication device 42. Although the communication device 42 is described as a mobile phone or personal digital assistant, it will be understood that the communication device 42 can be any of a variety of suitable devices that are capable of receiving and transmitting information or data. For example, the communication device 42 can be a device that is customized and designed specifically to function as the communication device 42 in the medication regimen monitoring system 110.

In one example, the communication device 42 can initiate communication with the RFID apparatus 14 by sending a signal to the RFID apparatus 14 that results in the RFID apparatus 14 responding with information or data regarding the detection of detectable agents or chemical markers in the person's biological material. In another example, the RFID apparatus 14 can sense that the communication device 42 is positioned proximate to the RFID apparatus 14 and initiate a signal to the communication device 42 with information or data regarding the detection of detectable agents or chemical markers in the person's biological material.

Once the communication device 42 receives information or data regarding the detection of detectable agents or chemical markers in the person's biological material, such information and data can be transmitted to medical professionals, caretakers, or other interested parties that are located remotely from the person. At any desired time, the person wearing the patch 12 can initiate the inspection of the person's biological material by moving the communication device 42 into close proximity of the patch 12 as shown in FIG. 3. Such proximity can direct the sensor 16 to inspect the person's biological material. Once the biological material is inspected, the sensor 16 can communicate the results of such an inspection to the RFID apparatus 14. The RFID apparatus 14 can then communicate the results to the communication device 42 such as through use of the antenna 26. In such an arrangement, the communication device 42 can function as an RFID reader. Once the results are received by the communication device 42, the results can be further transmitted to a remote location for immediate viewing by the medical professional or caregiver or stored for future viewing by the medical professional or caregiver.

When the communication device 42 is a mobile phone or a personal digital assistant, the results can be transmitted to the remote location in any of a variety of suitable formats. For example, the results can be transmitted as raw data, as a text message, as an electronic mail message, as a radio message, or in some other format. While the results can be transmitted using wireless technologies, the results can alternatively be transmitted by other suitable communication methods. For example, a communication device can be periodically linked to a computer that would then upload the results from the communication device and transmit them over an intranet or the Internet.

An inspection of the person's biological material can be initiated remotely by a medical professional or caregiver. For example, the medical professional or caregiver that would like to determine the person's compliance with the medical regimen can contact the person and request an inspection. Such contact can be achieved by the medical professional or caregiver initiating a call, sending an electronic mail, or sending a text message to the patient requesting the person to move the communication device 42 into proximity of the patch 12 to initiate the inspection. When the communication device 42 is a mobile phone or a personal digital assistant, the person can receive the request through the mobile phone or personal digital assistant and immediately initiate the inspection, with the results of the inspection transmitted back to the medical professional or caregiver.

In another example, an inspection of the person's biological material can be initiated remotely by a medical professional or caregiver sending a signal to the communication device 42 instructing the communication device 42 to automatically attempt the inspection. The communication device 42 can respond by sending a signal to the RFID apparatus 14 to initiate the inspection. The results of successful inspection can be transmitted back to the communication device 42 and further communicated to the medical professional or caregiver. In such an example, the person need not take any proactive actions and may not even be aware that inspection has occurred and the results have been communicated to the medical professional or caregiver.

Although this disclosure describes medical professionals, caregivers, law enforcement, other authorities or person's wearing the patch 12 as initiating the inspection of the person's biological material, it will be understood that such inspections can be automated. For example, the communication device 42 can be programmed to initiate inspections at set times or intervals. In another example, the RFID apparatus 14 can be programmed to initiate inspections at set times or intervals. In yet another example, a remote computer or other such remote device can be programmed to send signals to the communication device 42 to initiate inspections at set times or intervals.

In yet another example, a caregiver, medical professional or a remote computer can send a message requesting that medication is taken followed by, at a pre-defined interval, an instruction to initiate an inspection.

In a further embodiment, the person being monitored may be given a set of more than one medication, and the set of medications may include a multitude of detectable entities that can be discriminated from one another by the sensing device, or more than one sensing device, contained within the patch, so the implementation of a complex medication regime can be monitored.

Figure 4:
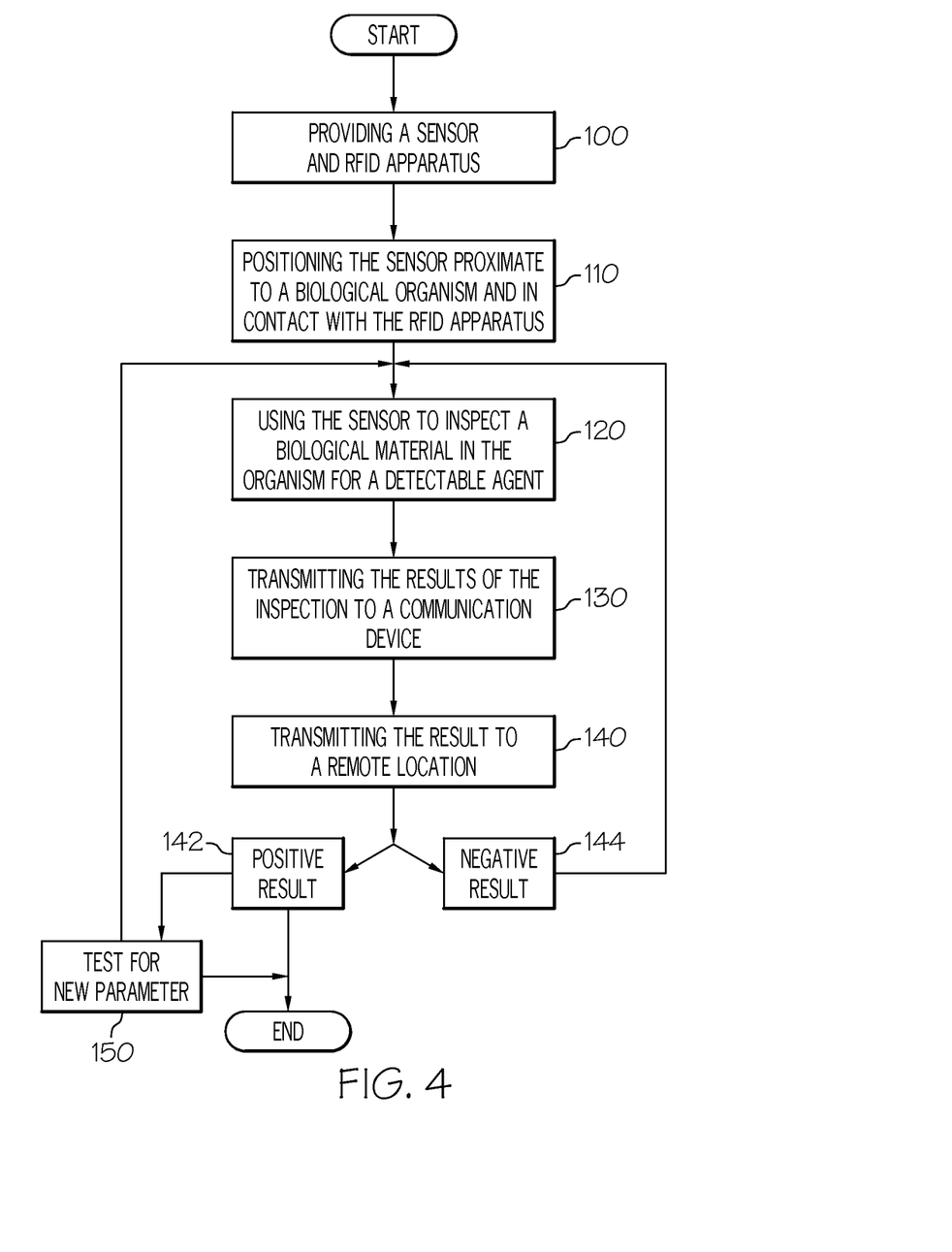
FIG. 4 is a block diagram providing an exemplary method of practicing the present invention.

Reference is now directed to FIG. 4 of the presently described invention in which a block diagram is provided showing an exemplary method of carrying out the invention. The process is started and at step 100 a sensor and RFID apparatus is provided. Next, the sensor is positioned proximate to a biological organism and in electrical contact with the RFID apparatus at step 110. Then, at step 120 the sensor is used to detect a biological material in the organism. At step 130, the result of the inspection is transmitted to a communication device and at step 140, the result is transmitted to a remote location. If a negative result is obtained as a result of the inspection and determined at step 144 the process is reinitiated by transmitting a further signal to the communication device and/or RFID apparatus and the process is repeated.

In situations where a positive result is obtained after the inspection then at step 142, the inspection can end or alternatively, a new request for an inspection of a different parameter can be requested at step 150.

In addition, it should be understood that the inspection can seek to locate multiple agents simultaneously, substantially simultaneously or to sequentially find agents or biological materials either as part of the original inspection request or as may be necessary based on the results of one or more inspections.

The foregoing description of examples has been presented for purposes of illustration and description. It is not intended to be exhaustive or limiting to the forms described. Numerous modifications are possible in light of the above teachings. Some of those modifications have been discussed, and others will be understood by those skilled in the art. The examples were chosen and described in order to best illustrate principles of various examples as are suited to particular uses contemplated. The scope is, of course, not limited to the examples set forth herein, but can be employed in any number of applications and equivalent devices by those of ordinary skill in the art.

What is claimed is:

1. A system for monitoring compliance with a medication regimen comprising:
   a patch and an RFID transceiver;
   the patch includes an RFID apparatus and a sensor and the patch is configured to be removably securable to a body of a biological organism;
   the sensor is in electrical communication with the RFID apparatus and is configured to inspect for the presence of at least one biological material of a biological organism for the presence of a detectable agent;
   the RFID apparatus is configured to communicate a result of the inspection to the RFID transceiver;
   the RFID transceiver is configured to receive the results of the inspection and is further configured to transmit the results of the inspection to a server or remote location;
   the RFID transceiver is configured to request a further inspection after the step of transmitting the result to the RFID transceiver;
   the server or remote location configured to determine a positive or negative result after receiving the result of the inspection;
   the server or remote location is configured to request a new inspection of a different parameter based on a positive result and the server or remote location is configured to reinitiate the inspection by transmitting a further signal to the RFID apparatus based on a negative result;
   wherein the RFID apparatus and/or RFID transceiver includes a memory portion;
   wherein the memory portion can store results of successive inspections and determine a compliance profile; and
   wherein the system is configured to initiate inspection by at least one of the following:
   the RFID transceiver initiates an inspection each time the biological organism comes within range of the RFID transceiver,
   the RFID transceiver initiates inspections at set times or intervals, and
   the RFID apparatus initiates communication at the set times or intervals from the RFID transceiver.

2. The system as recited in claim 1, wherein the detectable agent is selected from a group including a chemical marker, food component, food, food-safe additive or combinations thereof.

3. The system as recited in claim 2, wherein the food safe additive is selected from a group including a protein, oil, flavoring, or other suitable chemical or combination thereof.

4. The system as recited in claim 2, wherein the food is selected from a group including dairy products, sugary foods, fruits or vegetables or combinations thereof.

5. The system as recited in claim 4, wherein the vegetable is asparagus.

6. The system as recited in claim 1, wherein the biological material is selected from a group including perspiration, exhalations, blood, tears, urine, excretions, saliva and combinations thereof.

7. A system for monitoring compliance with a medication regimen comprising:
a patch and a communication device, the patch includes an RFID apparatus and a sensor;
the patch is configured to be removably securable to a body of a biological organism and the sensor is in electrical communication with the RFID apparatus and is configured to inspect for the existence of at least one biological material of a biological organism for the presence of a detectable agent;
the RFID apparatus is configured to communicate a result of the inspection to the communication device;
the communication device is configured to receive the results of the inspection and is further configured to transmit the results of the inspection to a server or remote location;
the communication device and the server or remote location are configured to request a further inspection of the result;
the server or remote location is configured to determine a positive or negative result after receiving the result of the inspection;
the server or remote location is configured to request a new inspection of a different parameter based on a positive result and the server or remote location is configured to reinitiate the inspection by transmitting a further signal to the RFID apparatus based on a negative result;
wherein the RFID apparatus includes a memory portion;
wherein the memory portion can store results of successive inspections and determine a compliance profile; and
wherein the system is configured to initiate inspection by at least one of the following:
the communication device initiates an inspection each time the biological organism comes within range of the communication device,
the communication device initiates inspections at set times or intervals, and the RFID apparatus initiates communication at the set times or intervals.

8. The system as provided in claim 7, wherein the RFID apparatus includes a power source.

9. The system as provided in claim 8, wherein the power source is selected from a group including a battery, capacitor, power antenna or combinations thereof.

10. The system as provided in claim 7, wherein the sensor is provided with at least one of a light emitting diode or infra-red radiation source.

11. The system as provided in claim 7, wherein the sensor may inspect for multiple biological materials.

12. The system as provided in claim 11, wherein the inspection for multiple biological materials is done simultaneously.

13. The system as provided in claim 11, wherein the inspection for multiple biological materials is done sequentially.

14. A method for monitoring compliance with a medication regimen comprising the steps of:
providing a sensor and a RFID apparatus;
positioning the sensor proximate to a biological organism, where the sensor is in electrical communication with the RFID apparatus;
using the sensor to inspect for the presence of at least one biological material of a biological organism for the presence of a detectable agent;
transmitting with the RFID apparatus a result of the inspection to an RFID transceiver;
providing a server or remote location configured to determine a positive or negative result after receiving the result of the inspection;
the RFID transceiver receiving the results of the inspection and transmitting the results of the inspection to the server or remote location;
requesting a further inspection after the step of transmitting the result to the RFID transceiver;
wherein the server or remote location is configured to request a new inspection of a different parameter based on a positive result and the server or remote location is configured to reinitiate the inspection by transmitting a further signal to the RFID apparatus based on a negative result;
wherein the RFID apparatus and/or RFID transceiver includes a memory portion; and
wherein the memory portion stores results of successive inspections and determines a compliance profile
the inspection is initiated by at least one of the following:
the RFID transceiver initiates an inspection each time the biological organism comes within range of the RFID transceiver,
the RFID transceiver initiates inspections at set times or intervals, and
the RFID apparatus initiates communications at the set times or intervals.

15. The method as recited in claim 14, wherein the detectable agent is selected from a group including a chemical marker, food component, a food, a food-safe additive or combinations thereof.

16. The method as recited in claim 15, wherein the food safe additive is selected from a group including a protein, oil, flavoring, or other suitable chemical or combination thereof.

17. The method as recited in claim 15, wherein the food is selected from a group including dairy product, sugary foods, fruits or vegetables or combinations thereof.

18. The method as recited in claim 17, wherein the vegetable is asparagus.

19. The method as recited in claim 14, wherein the biological material is selected from a group including perspiration, exhalations, blood, tears, urine, excretions, saliva and combinations thereof.

20. The method as recited in claim 14, wherein the RFID apparatus includes a transceiver.

21. The method as recited in claim 20, including a further step of initiating the inspection when the biological organism is in close proximity to the RFID apparatus after the step of providing the sensor and RFID apparatus.

22. A method for monitoring compliance with a medication regimen comprising the steps of:
providing a sensor and an RFID apparatus;
positioning the sensor proximate to a biological organism, where the sensor is in electrical communication with the RFID apparatus;
using the sensor to inspect for the presence of at least one biological material of the biological organism for the presence of a detectable agent;
transmitting with the RFID apparatus a result of the inspection to a communication device;

providing a server or remote location configured to determine a positive or negative result after receiving the result of the inspection;

transmitting the result of the inspection to the server or remote location;

requesting a further inspection after the step of transmitting the result to the remote location;

wherein the server or remote location is configured to request a new inspection of a different parameter based on a positive result and the server or remote location is configured to reinitiate the inspection by transmitting a further signal to the RFID apparatus based on a negative result;

wherein the RFID apparatus includes a memory portion;

wherein the memory portion stores results of successive inspections and determines a compliance profile, and the inspection is initiated by at least one of the following:

the communication device initiates an inspection each time the biological organism comes within range of the communication device, the communication device initiates inspections at set times or intervals, and the RFID apparatus initiates communications at the set times or intervals.

23. The method as provided in claim 22, including a further step of analyzing the result to determine a positive or negative result after the step of transmitting the result to a location.

24. The method as provided in claim 23, including a further step of requesting a new inspection based on a positive analysis after the step of analyzing the result.

25. The method as provided in claim 23, including a further step of requesting a repeat of the previous inspection based on a negative analysis after the step of analyzing the result.

26. The method as provided in claim 22, wherein the step of using the sensor to inspect is done to seek multiple biological materials.

27. The method as provided in claim 26, wherein the inspection for multiple biological materials is done simultaneously.

28. The method as provided in claim 26, wherein the inspection for multiple biological materials is done sequentially.

29. The system of claim 1, wherein the inspections are initiated at set times or intervals by the RFID transceiver or RFID apparatus.

* * * * *